(12) United States Patent
Morgan et al.

(10) Patent No.: US 8,304,232 B2
(45) Date of Patent: Nov. 6, 2012

(54) PHOTOBIOREACTORS, SOLAR ENERGY GATHERING SYSTEMS, AND THERMAL CONTROL METHODS

(75) Inventors: Frederick M. Morgan, Canton, MA (US); Stuart A. Jacobson, Lexington, MA (US); Johan van Walsem, Acton, MA (US)

(73) Assignee: Joule Unlimited Technologies, Inc., Bedford, MA (US)

(*) Notice: Subject to any disclaimer, the term of this patent is extended or adjusted under 35 U.S.C. 154(b) by 0 days.

(21) Appl. No.: 13/128,365

(22) PCT Filed: Jul. 28, 2010

(86) PCT No.: PCT/US2010/043573
§ 371 (c)(1),
(2), (4) Date: May 9, 2011

(87) PCT Pub. No.: WO2011/017171
PCT Pub. Date: Feb. 10, 2011

(65) Prior Publication Data
US 2011/0217692 A1 Sep. 8, 2011

Related U.S. Application Data

(60) Provisional application No. 61/322,192, filed on Apr. 8, 2010, provisional application No. 61/271,904, filed on Jul. 28, 2009.

(51) Int. Cl.
*A01G 7/00* (2006.01)
*A01G 9/00* (2006.01)
*A01H 13/00* (2006.01)
*C12P 1/00* (2006.01)
*C12N 1/12* (2006.01)
*C12M 1/00* (2006.01)
*C12M 3/00* (2006.01)

(52) U.S. Cl. .......... 435/292.1; 47/1.4; 47/17; 435/289.1; 435/257.1; 435/41

(58) Field of Classification Search ............... 435/292.1, 435/41, 257.1, 289.1; 47/1.4, 17
See application file for complete search history.

(56) References Cited

U.S. PATENT DOCUMENTS

| 3,955,317 A | 5/1976 | Gudin |
| 4,198,953 A | 4/1980 | Power |
| 4,360,005 A | 11/1982 | Sharpe |
| 4,390,624 A | 6/1983 | Leavitt |

(Continued)

FOREIGN PATENT DOCUMENTS

CN 201180138 Y 1/2009

(Continued)

OTHER PUBLICATIONS

Patent Cooperation Treaty, International Search Report and Written Opinion dated Dec. 28, 2010, PCT/US2010/043573.

(Continued)

*Primary Examiner* — Nathan Bowers
*Assistant Examiner* — Lydia Edwards
(74) *Attorney, Agent, or Firm* — Chang B. Hong, Esq.

(57) ABSTRACT

The present invention provides photobioreactors, solar energy gathering systems, and methods for thermal control of a culture medium containing a prototrophic organism in a photobioreactor, that allow temperature control in a cost effective manner, reducing the energy required for temperature control of a culture medium containing phototrophic microorganisms in a photobioreactor.

4 Claims, 14 Drawing Sheets

U.S. PATENT DOCUMENTS

| | | | |
|---|---|---|---|
| 4,868,123 A * | 9/1989 | Berson et al. | 435/286.6 |
| 4,952,511 A | 8/1990 | Radmer | |
| 4,970,166 A | 11/1990 | Mori | |
| 5,104,803 A | 4/1992 | Delente | |
| 5,151,347 A | 9/1992 | Delente et al. | |
| 5,162,051 A | 11/1992 | Hoeksema | |
| 5,164,308 A | 11/1992 | Kyle | |
| 5,338,673 A | 8/1994 | Thepenier et al. | |
| 5,534,417 A | 7/1996 | Arad et al. | |
| 5,614,378 A | 3/1997 | Yang et al. | |
| 5,846,816 A * | 12/1998 | Forth | 435/292.1 |
| 5,958,761 A | 9/1999 | Yogev et al. | |
| 5,981,271 A | 11/1999 | Doucha et al. | |
| 5,992,508 A * | 11/1999 | Lowenstein et al. | 165/46 |
| 6,022,701 A | 2/2000 | Boussiba et al. | |
| 6,174,720 B1 | 1/2001 | Oxley et al. | |
| 6,492,149 B1 | 12/2002 | Muller-Feuga | |
| 6,492,799 B1 | 12/2002 | Rajala et al. | |
| 6,509,188 B1 | 1/2003 | Trösch et al. | |
| 6,602,703 B2 | 8/2003 | Dutil | |
| 6,603,069 B1 | 8/2003 | Muhs et al. | |
| 7,374,928 B2 | 5/2008 | Trösch | |
| 7,618,813 B2 | 11/2009 | Lee et al. | |
| 7,682,821 B2 | 3/2010 | Woods et al. | |
| 2003/0017558 A1 | 1/2003 | Pham et al. | |
| 2003/0059932 A1 | 3/2003 | Craigie et al. | |
| 2003/0073231 A1 | 4/2003 | Dutil | |
| 2003/0228684 A1 | 12/2003 | Burbidge et al. | |
| 2004/0048364 A1 | 3/2004 | Trösch | |
| 2005/0064577 A1 | 3/2005 | Berzin | |
| 2005/0239182 A1 | 10/2005 | Berzin | |
| 2005/0260553 A1 | 11/2005 | Berzin | |
| 2005/0279095 A1 | 12/2005 | Goldman | |
| 2006/0033222 A1 | 2/2006 | Godfrey et al. | |
| 2006/0035370 A1 | 2/2006 | Lee et al. | |
| 2007/0048848 A1 | 3/2007 | Sears | |
| 2007/0048859 A1 | 3/2007 | Sears | |
| 2007/0104761 A1 | 5/2007 | Williams | |
| 2007/0114476 A1 | 5/2007 | Williams | |
| 2007/0289206 A1 | 12/2007 | Kertz | |
| 2008/0009055 A1 | 1/2008 | Lewnard | |
| 2008/0018964 A1 | 1/2008 | Li et al. | |
| 2008/0086939 A1 | 4/2008 | Dunlop et al. | |
| 2008/0096267 A1 | 4/2008 | Howard et al. | |
| 2008/0153080 A1 | 6/2008 | Woods et al. | |
| 2008/0160591 A1 | 7/2008 | Willson et al. | |
| 2008/0160593 A1 | 7/2008 | Oyler | |
| 2008/0178739 A1 | 7/2008 | Lewnard et al. | |
| 2008/0219010 A1 | 9/2008 | Oyama | |
| 2008/0220515 A1 | 9/2008 | McCall | |
| 2008/0274494 A1 | 11/2008 | Kertz | |
| 2008/0286851 A1 | 11/2008 | Whitton | |
| 2008/0293132 A1 | 11/2008 | Goldman et al. | |
| 2008/0299063 A1 | 12/2008 | Howard et al. | |
| 2009/0011492 A1 | 1/2009 | Berzin | |
| 2009/0047722 A1 | 2/2009 | Wilkerson et al. | |
| 2009/0077864 A1 | 3/2009 | Marker et al. | |
| 2009/0081743 A1 | 3/2009 | Hazelbeck et al. | |
| 2009/0098637 A1 | 4/2009 | Muir et al. | |
| 2009/0113790 A1 | 5/2009 | Erd | |
| 2009/0130706 A1 * | 5/2009 | Berzin et al. | 435/41 |
| 2009/0151241 A1 | 6/2009 | Dressler et al. | |
| 2009/0181434 A1 | 7/2009 | Aikens et al. | |
| 2009/0181438 A1 | 7/2009 | Sayre | |
| 2009/0203067 A1 | 8/2009 | Eckerle et al. | |
| 2009/0215139 A1 | 8/2009 | Datta et al. | |
| 2009/0291490 A1 | 11/2009 | Spradling | |
| 2009/0305388 A1 | 12/2009 | Dressler et al. | |
| 2010/0028976 A1 | 2/2010 | Hu et al. | |
| 2010/0043883 A1 | 2/2010 | Yu et al. | |
| 2010/0047122 A1 | 2/2010 | Barringer, Jr. | |
| 2010/0055765 A1 | 3/2010 | Frank | |
| 2010/0144019 A1 | 6/2010 | Hsu | |

FOREIGN PATENT DOCUMENTS

| | | | |
|---|---|---|---|
| CN | 201258325 Y | 6/2009 | |
| EP | 0 786 825 A1 | 7/1997 | |
| EP | 1 995 304 A1 | 11/2008 | |
| FR | 2 564 854 A1 | 11/1985 | |
| GB | 2 182 076 A | 5/1987 | |
| JP | 10 304872 A | 11/2008 | |
| KR | 2001 079 126 A | 8/2001 | |
| KR | 20090041855 A | 4/2009 | |
| RU | 86395 U | 9/2009 | |
| WO | WO 91/08314 A1 | 6/1991 | |
| WO | WO 96/21723 A1 | 7/1996 | |
| WO | WO 99/15620 A1 | 4/1999 | |
| WO | WO 03/094598 A1 | 11/2003 | |
| WO | WO 2005/006838 A2 | 1/2005 | |
| WO | WO 2005/101525 A2 | 10/2005 | |
| WO | WO 2005/104819 A1 | 11/2005 | |
| WO | WO 2006/020802 A2 | 2/2006 | |
| WO | WO 2007/025145 A2 | 3/2007 | |
| WO | WO 2007/070452 A1 | 6/2007 | |
| WO | WO 2007/098150 A2 | 8/2007 | |
| WO | WO 2007/147028 A2 | 12/2007 | |
| WO | WO 2008/008262 A2 | 1/2008 | |
| WO | WO 2008/010737 A1 | 1/2008 | |
| WO | WO 2008/055190 A2 | 5/2008 | |
| WO | WO 2008/076998 A1 | 6/2008 | |
| WO | WO 2008/083352 A1 | 7/2008 | |
| WO | WO 2008/134010 A2 | 11/2008 | |
| WO | WO 2008/143775 A2 | 11/2008 | |
| WO | WO 2008/151376 A1 | 12/2008 | |
| WO | WO 2009/002772 A2 | 12/2008 | |
| WO | WO 2009/007646 A2 | 1/2009 | |
| WO | WO 2009/040383 A1 | 4/2009 | |
| WO | WO 2009/087567 A2 | 7/2009 | |
| WO | WO 2009/090549 A2 | 7/2009 | |
| WO | WO 2009/149519 A1 | 12/2009 | |
| WO | WO 2009/153790 A1 | 12/2009 | |
| WO | WO 2010/012028 A1 | 2/2010 | |
| WO | WO 2010/017002 A1 | 2/2010 | |
| WO | WO 2010/042484 A2 | 4/2010 | |
| WO | WO 2010/047815 A2 | 4/2010 | |
| WO | WO 2010/064780 A1 | 10/2010 | |

OTHER PUBLICATIONS

Pulz, O., "Photobioreactors: production systems for phototrophic microorganisms," *Appl. Microbiol. Biotechnol.*, 57: 287-293 (Jan. 2001).

Hu, Qiang, et al., "Optimal Tilt Angles of Enclosed Reactors for Growing Photoautotrophic Microorganisms Outdoors" *Journal of Fermentation and Bioengineering*, vol. 85, No. 2, 230-236, 1998.

Chisti, Yusuf, "Pneumatically agitated bioreactors in industrial and environmental bioprocessing: Hydrodynamics, hydraulics, and transport phenomena", ASME Reprint No. AMR 233, *Appl. Mech. Rev.*, vol. 51, No. 1, pp. 33-112, Jan. 1998.

Hu, Qiang, et al., "A Flat Inclined Modular Photobioreactor for Outdoor Mass Cultivation of Photoautotrophs", *Biotechnology and Bioengineering*, vol. 51, pp. 51-60, 1996.

Janssen, Marcel, et al., "Enclosed Outdoor Photobioreactors: Light Regime, Photosynthetic Efficiency, Scale-Up, and Future Prospects", *Biotechnology and Bioengineering*, vol. 81, No. 2, pp. 193-210, Jan. 20, 2003.

Hu, Qiang, et al, "Combined effects of light intensity, light path and culture density on output rate of *Spirulina platensis* (Cyanobacteria)", *European Journal of Phycology*, vol. 33, pp. 165-171, 1998.

Hu, Qiang, et al, "Optimal tilt angles of enclosed reactors for growing photoautotrophic microorganisms outdoors", *Journal of Fermentation and Bioengineering*, vol. 85, No. 2, pp. 230-236, 1998.

Hu, Qiang, et al, "A flat inclined modular photobioreactor for outdoor mass cultivation of photoautotrophs", *Biotechnology and Bioengineering*, vol. 51 pp. 51-60, 1996.

Hu, Qiang and Richmond, Amos, "Productivity and photosynthetic efficiency of *Spirulina platensis* as affected by light intensity, algal density and rate mixing in a flat plate photobioreactor", *Journal of Applied Phycology*, vol. 8, pp. 139-145, 1996.

Merchuck, J.C., et al., "Photobioreactor design and Fluid Dynamics", *Chemical and Biochemical Engineering Quarterly*, vol. 21, No. 4, pp. 345-355, 2007.

Richmond, Amos, et al., "Efficient use of strong light for high photosynthetic productivity: interrelationships between the optical path, the optimal populatiuon density and cell-growth inhibition", *Biomolecular Engineering*, vol. 20, pp. 229-236, 2003.

Wu, Xiaoxi and Merchuk, Jose C. "A model integrating fluid dynamics in photosynthesis and photoinhibition processes" *Chemical Engineering Science*, vol. 56, pp. 3527-3538, 2001.

Grima, Molina E., et al., "Photobioreactors: light regime, mass transfer, and scaleup," *Journal of Biotechnology*, vol. 70, pp. 231-247, 1999.

Notification Concerning Transmittal of International Preliminary Report on Patentability for International Application No. PCT/US2010/043573 dated Feb. 9, 2012.

\* cited by examiner

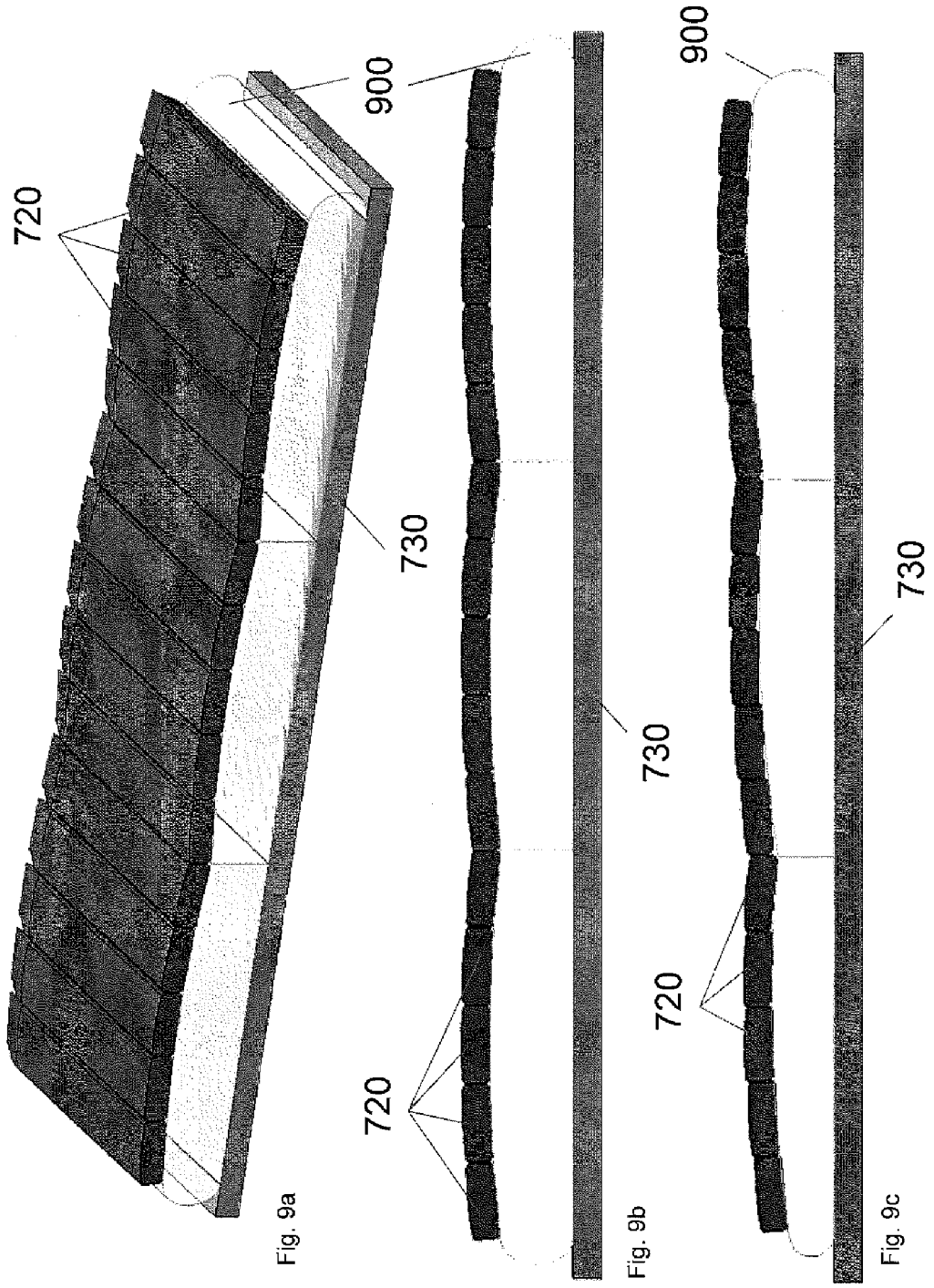

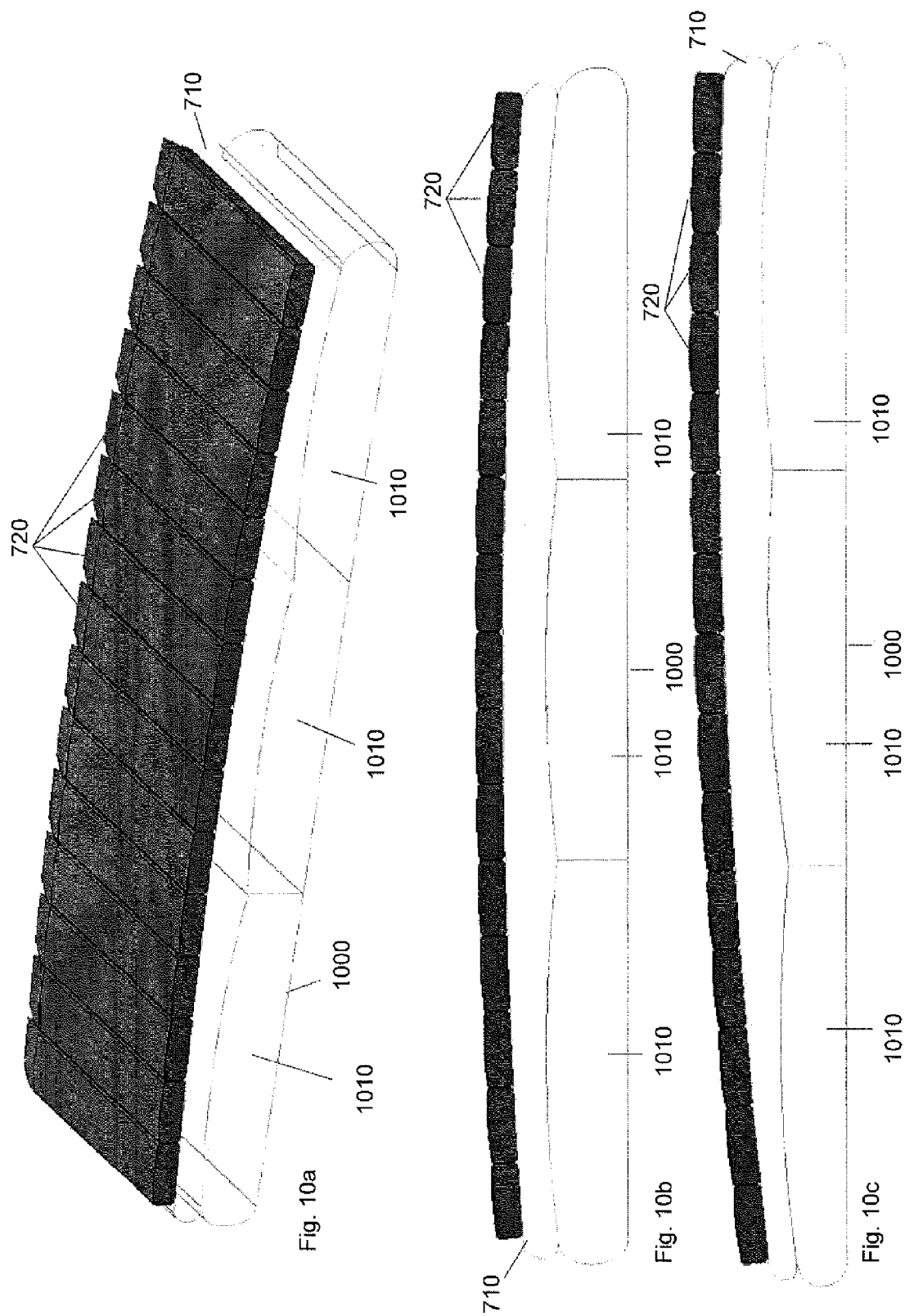

US 8,304,232 B2

PHOTOBIOREACTORS, SOLAR ENERGY GATHERING SYSTEMS, AND THERMAL CONTROL METHODS

RELATED APPLICATIONS

This application is the U.S. National Stage of International Application No. PCT/US2010/043573, filed Jul. 28, 2010, which designates the U.S., published in English, and claims the benefit of U.S. Provisional Application No. 61/322,192, filed Apr. 8, 2010, and U.S. Provisional Application No. 61/271,904, filed on Jul. 28, 2009. The entire teachings of the above applications are incorporated herein by reference.

BACKGROUND OF THE INVENTION

As the world's energy demands increase and energy production from non-renewable sources becomes more expensive, difficult, and harmful to the environment, the desire to capture energy from the sun has correspondingly increased.

Photobioreactors employing sunlight have been described for the production of biofuels from microorganisms. Suitable microorganisms, typically, phototrophic microorganisms, are grown or propagated in these photobioreactors using solar energy for the production of biomass or the production of specific compounds. Growth of phototrophic microorganisms and production of specific compounds, for example, ethanol, using phototrophic microorganisms is temperature dependent. Further, heat mitigation problems, for example, caused by exposure of a culture of phototrophic microorganisms to infrared radiation leading to elevated temperatures that are not optimal, are common, and active temperature control requires a significant amount of energy that reduces the net energy generating capability.

There is, therefore, a need for systems, apparatuses and methods that allow temperature control in a cost effective manner, reducing the energy required for temperature control of a culture medium containing phototrophic microorganisms in a photobioreactor.

SUMMARY OF THE INVENTION

One embodiment of the present invention is a photobioreactor. The photobioreactor includes (a) a reactor chamber for enclosing a phototrophic microorganism and culture medium therefor and (b) a heat energy system. At least part of the reactor chamber is transparent for light of a wavelength that is photosynthetically active in the phototrophic microorganism, and the reactor chamber and heat energy system are in controllable thermal contact.

Another embodiment is a photobioreactor that comprises (a) a reactor chamber for enclosing a phototrophic microorganism and culture medium therefor, (b) a heat exchange chamber for containing a heat exchange fluid, and (c) a thermal control layer between the reactor chamber and the heat exchange chamber. At least part of the reactor chamber is transparent for light of a wavelength that is photosynthetically active in the phototrophic microorganism, and the thermal control layer abuts the reactor chamber on a first side of the thermal control layer and abuts the heat exchange volume on a second side of the thermal control layer, and the thermal control layer is adapted to control heat exchange between the culture medium and the heat exchange fluid.

Another embodiment is a solar energy gathering system. The system comprises (a) a photobioreactor that includes (i) a reactor chamber for enclosing a phototrophic microorganism and culture medium therefore and (ii) a heat exchange chamber for containing a heat exchange fluid. The reactor chamber and the heat exchange chamber are in controllable thermal contact. The system also comprises (b) a cooling device adapted for controlled cooling of the heat exchange fluid. At least part of the reactor chamber is transparent for light of a wavelength that is photosynthetically active in the phototrophic microorganism.

Another embodiment is a method for thermal control of a culture medium containing a phototrophic organism in a photobioreactor. The method includes: (a) measuring the temperature of the culture medium contained in a reactor chamber of the photobioreactor, the reactor chamber being positioned substantially horizontally to provide a headspace above the liquid culture; wherein at least part of the reactor chamber is transparent for light of a wavelength that is photosynthetically active in the phototrophic microorganism, (b) measuring the temperature of a heat exchange liquid contained in a heat exchange chamber, the heat exchange chamber and the reactor chamber being structurally coupled to a thermal control layer, the thermal control layer being positioned between the heat exchange chamber and the reactor chamber; wherein the thermal control layer is adapted to contain a fluid, (c) determining if a change in thermal contact between the reactor chamber and the heat exchange chamber is desired, and (d) changing fluid presence in the thermal control layer if a change in thermal contact is desired.

Another embodiment is a photobioreactor that includes (a) a reactor chamber for enclosing a phototrophic microorganism and culture medium therefor, and (b) a heat exchange chamber for containing a heat exchange liquid. At least part of the reactor chamber is transparent for light of a wavelength that is photosynthetically active in the phototrophic microorganism, and the reactor chamber and heat exchange chamber are in thermal contact substantially through a separating layer.

Yet another embodiment is a solar energy gathering system that includes (a) a photobioreactor. The photobioreactor includes (i) a reactor chamber for enclosing a phototrophic microorganism and culture medium therefor; and (ii) a heat exchange chamber for containing a heat exchange fluid, wherein the reactor chamber and heat exchange chamber are in thermal contact substantially through a separating layer. The system further includes (b) a cooling device adapted for controlled cooling and/or exchange of heat exchange fluid. At least part of the reactor chamber is transparent for light of a wavelength that is photosynthetically active in the phototrophic microorganism.

The present invention provides systems, apparatuses and methods that allow temperature control in a cost effective manner, reducing the energy required for temperature control of a culture medium containing phototrophic microorganisms in a photobioreactor.

BRIEF DESCRIPTION OF THE DRAWINGS

FIG. 7a provides a perspective view of a section of a photobioreactor panel in which an inflatable thermal control layer is inflated to thermally isolate an array of linked reactor chambers from a heat energy system FIG. 7b provides a cross-sectional view of the photobioreactor panel in FIG. 7a.

FIG. 8a provides a perspective view of a section of a photobioreactor panel in which an inflatable thermal control layer is deflated to allow thermal contact of an array of linked reactor chambers with a heat energy system.

FIG. 8b provides a cross-sectional view of the photobioreactor panel in FIG. 8a.

FIG. 9a provides a perspective view of a section of a photobioreactor panel in which an inflatable sectioned (with three volumes) thermal control layer is filled with a liquid to allow thermal contact of an array of linked reactor chambers with a heat energy system.

FIG. 9b provides a cross-sectional view of the photobioreactor panel in FIG. 9a.

FIG. 9c provides a cross-sectional view of the photobioreactor panel in FIG. 9a, in which the sections/volumes are filled to different extents leading to a tilt of the reactor chambers.

FIG. 10a provides a perspective view of a section of a photobioreactor panel in which an inflatable thermal control layer is sandwiched between reactor chambers and a heat energy system including three inflatable heat exchange chambers that can be filled separately with liquid.

FIG. 10b provides a cross-sectional view of the photobioreactor panel in FIG. 10a.

FIG. 10c provides a cross-sectional view of the photobioreactor panel in FIG. 10a, in which the sections/volumes of the heat energy system are filled to different extents leading to a tilt of the reactor chambers.

DETAILED DESCRIPTION OF THE INVENTION

A description of preferred embodiments of the invention follows. While this invention has been particularly shown and described with references to preferred embodiments thereof, it will be understood by those skilled in the art that various changes in form and details can be made therein without departing from the scope of the invention encompassed by the appended claims.

The following explanations of terms and methods are provided to better describe the present invention and to guide those of ordinary skill in the art in the practice of the present invention. As used herein, "comprising" means "including" and the singular forms "a" or "an" or "the" include plural references unless the context clearly dictates otherwise. For example, reference to "comprising a phototrophic microorganism" includes one or a plurality of such phototrophic microorganisms. The term "or" refers to a single element of stated alternative elements or a combination of two or more elements, unless the context clearly indicates otherwise.

Unless explained otherwise, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and not intended to be limiting. Other features of the invention are apparent from the following detailed description and the claims.

Figure 1:
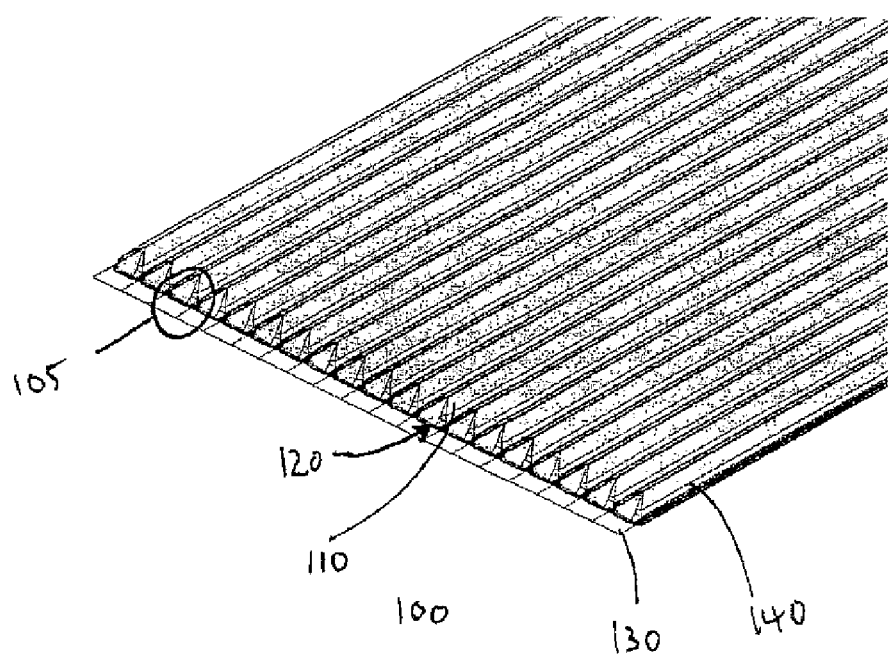
FIG. 1 is a perspective view of a section of a thin film photobioreactor panel.

In accordance with the present invention, according to certain embodiments, a section of an illustrative thin-film photobioreactor panel is shown in FIG. 1. The thin-film photobioreactor panel 100 includes 19 segments 105 each including a parallel reactor chambers 110 in the form of channels (top side) and corresponding heat exchange chambers 120 (bottom side) separated from the reactor chambers by a separating layer 130. The photobioreactor panel 100 can include further elements (not shown) such as inlets and outlets, for example, for growth media, carbon sources (e.g., $CO_2$), and probe devices such as optical density measurement device and thermometers. These elements can conveniently be located in headers (not shown) that can be structurally coupled to the photobioreactor panels. Typically, the photobioreactor panel 100 is made of thin-film polymer material as described below.

The reactor chambers of the photobioreactor 100 are shown to enclose a phototrophic microorganism and culture medium therefor 140, such as algae or cyanobacteria.

Figure 2:
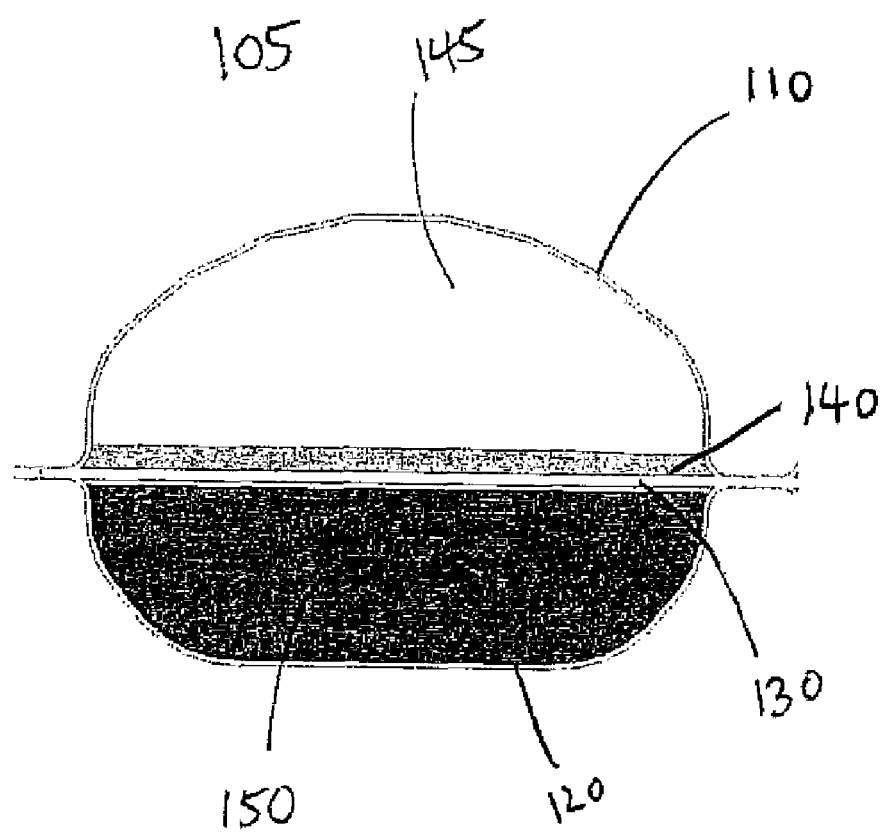
FIG. 2 is a cross-sectional view of one of the channels of the photobioreactor panel of FIG. 1.

In FIG. 2 a cross-sectional view of one segment 105 or channel of a photobioreactor panel section shown in FIG. 1 is illustrated. Both, the reactor chamber 110 and the heat exchange chamber 120 are provided by a thin-film material enclosure, typically, made from a polymeric material. The reactor chamber is shown with culture medium 140 and headspace 145 which allows, for example, flowing of carbon dioxide for the phototrophic microorganism and, generally, gas flow, for example air flow for cooling purposes. The separating layer 130 separates the reactor chamber from the heat exchange chamber 120, and thereby the culture medium 140 from heat exchange liquid 150. In other embodiments, the heat exchange chamber 120 containing heat exchange liquid 150 can be replaced with a solid material of high heat capacity.

Figure 3:
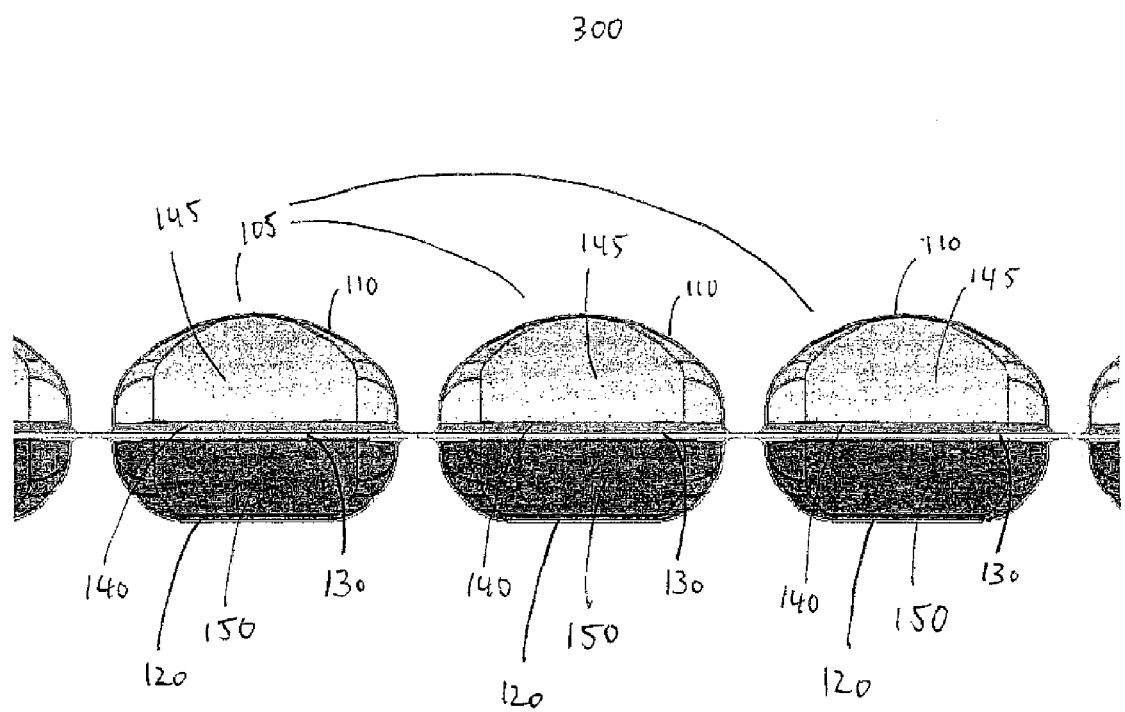
FIG. 3 is a cross-sectional view of three of the channels of the photobioreactor panel of FIG. 1.

FIG. 3 is a cross-sectional view 300 of three segments 105 or channels of the photobioreactor panel illustrated in FIG. 1.

Figure 4:
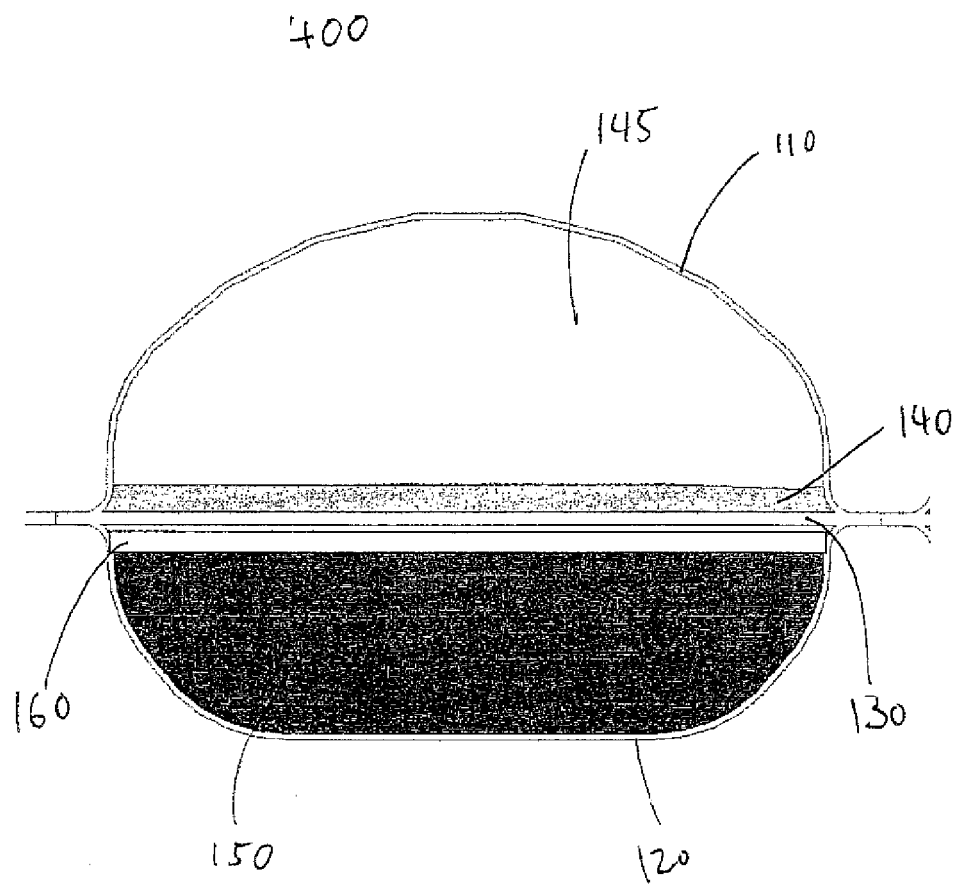
FIG. 4 is a cross-sectional view of a reactor chamber of a photobioreactor panel including an independent thermal control layer for controlled thermal contact between the thin-film reactor chamber and a corresponding thin-film heat exchange chamber.

In FIG. 4 a cross-sectional view of one segment or channel of a thin-film photobioreactor is shown. As in FIG. 2, the reactor chamber 110 and the heat exchange chamber 120 are provided by a thin-film material enclosure, typically, made from a polymeric material. The reactor chamber is shown with culture medium 140 and headspace 145 which allows, for example, flowing of carbon dioxide for the phototrophic microorganism and, generally, gas flow, for example air flow for cooling purposes. The separating layer 130 separates the reactor chamber from the heat exchange chamber 120, and thereby the culture medium 140 from heat exchange liquid 150. In addition to the embodiment illustrated in FIG. 2, the embodiment illustrated in FIG. 4 includes a thermal control layer 160 providing controllable thermal contact between the reactor chamber and the heat exchange volume. In typical embodiments, a photobioreactor panel includes a plurality of such segments or channels 400, each including a thermal control layer 160, and the thermal control layers can be designed to function independently to allow independent thermal control in each of the segments, and/or designed to function essentially as one thermal control layer by establishing appropriate fluid communication between the thermal control layers of each segment of the photobioreactor panel.

Figure 5:
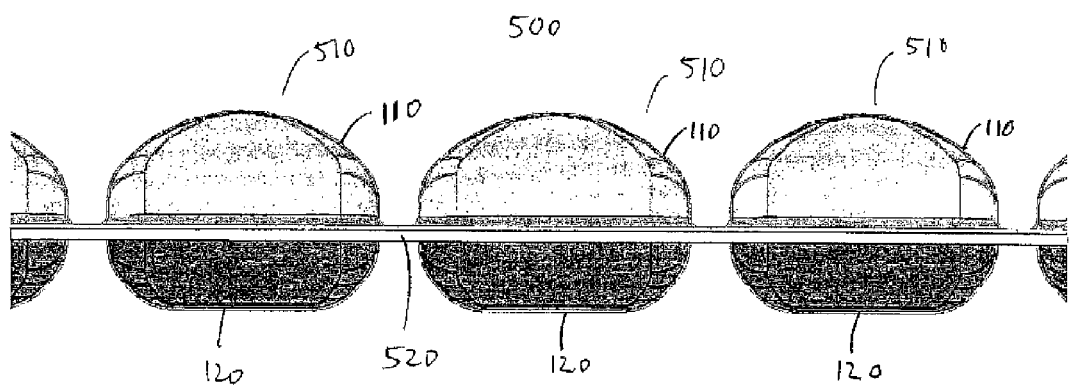
FIG. 5 is a cross-sectional view of three channels of a photobioreactor panel including a thermal control layer that is shared by all of the channels, the thermal control layer providing controlled thermal contact between the shown thin-film reactor chambers and the thin-film heat exchange chamber.

FIG. 5 provides a cross-sectional view 500 of three segments or channels 510 of a photobioreactor including a thermal control layer 520 that is shared by all of the channels, the thermal control layer providing controlled thermal contact between the shown thin-film reactor chambers 110 and the thin-film heat exchange chambers 120.

Figure 6:
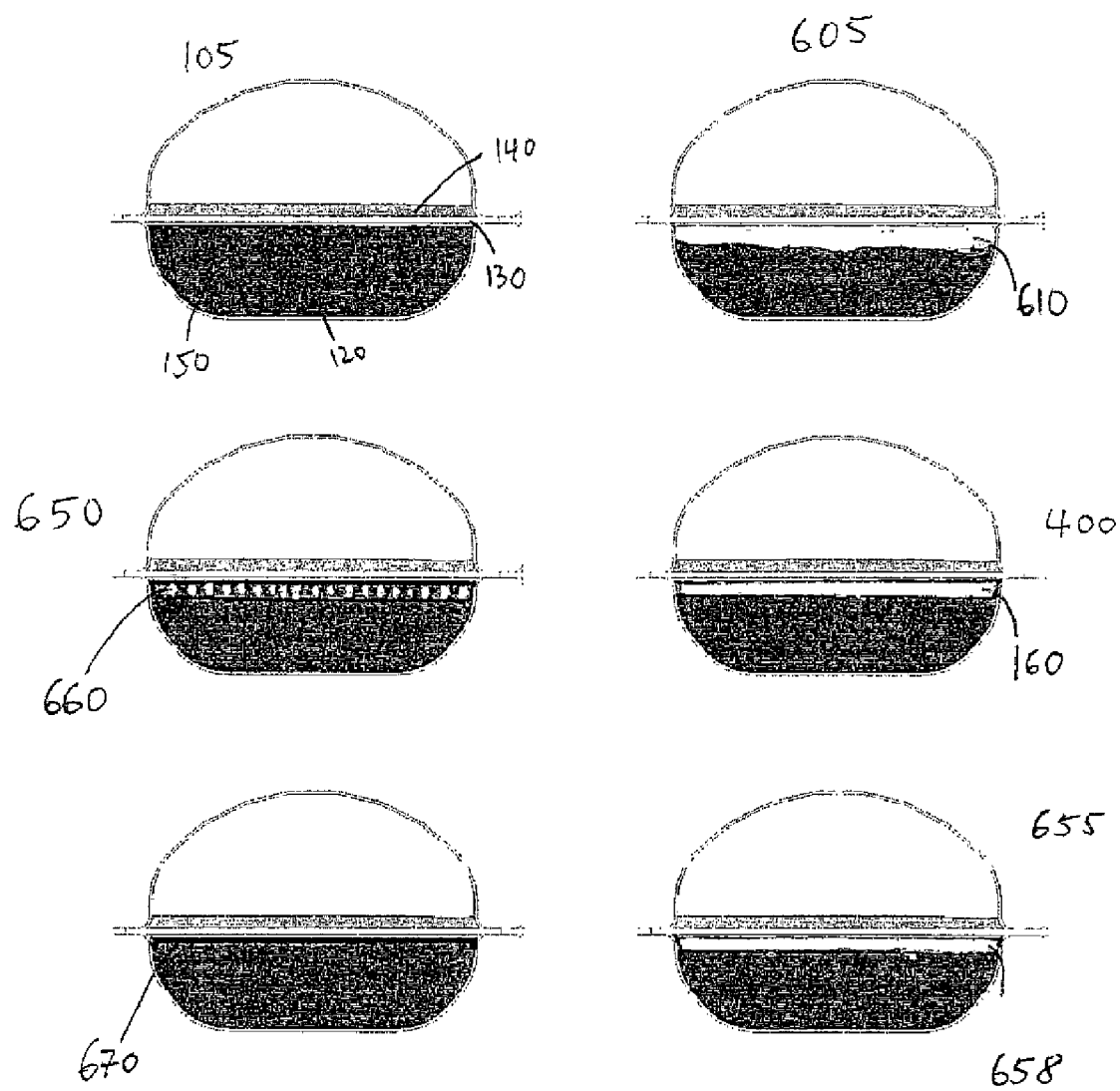
FIG. 6 provides cross-sectional views for segments of photobioreactor panel embodiments of the present invention, with thermal contact (segments on the left side) and with reduced or without thermal contact (segments on the right side).

FIG. 6 provides cross-sectional views for segments of photobioreactor embodiments of the present invention, with thermal contact (segments on the left side) and with reduced or without thermal contact (segments on the right side). Segment 105 is identical to the segment shown in FIG. 2. The heat exchange chamber as shown in this segment is in thermal contact through the separating layer 130. Heat exchange between the heat exchange liquid 150, typically, water and culture medium 140 containing phototrophic microorganisms is established. Heat exchange between the heat exchange liquid and culture medium can be reduced significantly, for example, by reducing the heat exchange liquid level in the heat exchange chamber to form an thermally insulating gas space 610 as shown for segment 605 which is structurally identical to segment 105. In some embodiments, controlling the extent of the gas space 610 within the heat exchange chamber can control the thermal contact between the reactor chamber and the heat exchange chamber (an example for a heat energy system), that is, a controllable thermal contact. Alternative embodiments are shown below. The segments 400 and 655 on the right include a thermal control layer which can be (a) structurally flexible 658 and filled with a fluid that is a good thermal insulator, for example a gas such as air, or (b) structurally stable 160 and filled with a fluid that is thermally insulating, for example a gas such as air, or even evacuated. In each of these cases thermal contact between the heat exchange chamber and the reactor chamber is reduced significantly. Thermal contact can than be increased by flowing a heat conducting fluid 660 (see dotted area), for example, water into the thermal control layer, as shown for segment 650. Alternatively, if the thermal control layer has a flexible enclosure as in 655 and contains a gas, deflating and thereby collapsing the flexible enclosure to a collapsed or deflated enclosure 670 can increase the thermal contact. The above embodiments illustrate different photobioreactor panel sections in which the reactor chamber and heat energy system are in controllable thermal contact.

Figure 7A:
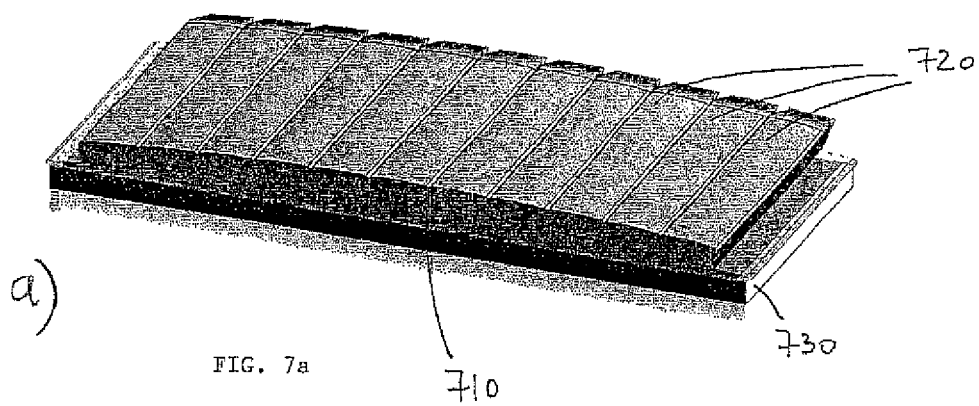
Figure 7B:
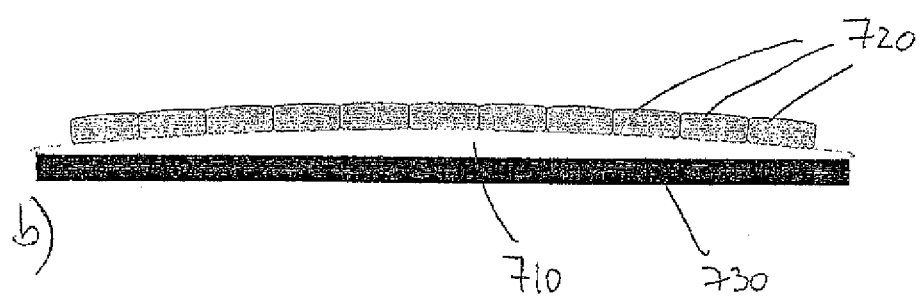

FIG. 7a provides a perspective view of a section of a photobioreactor panel in which an inflatable thermal control layer 710 (e.g., a flexible polymeric enclosure) is in an inflated state (e.g., filled with air to form an air filled bladder) to thermally isolate an array of linked reactor chambers 720 (e.g., enclosures made of polymeric material) from a heat energy system 730 (typically functioning as a thermal sink during day-time operation and as heat source during night-time operation). The corresponding cross-sectional view is shown in FIG. 7b.

Figures 8A, 8B:
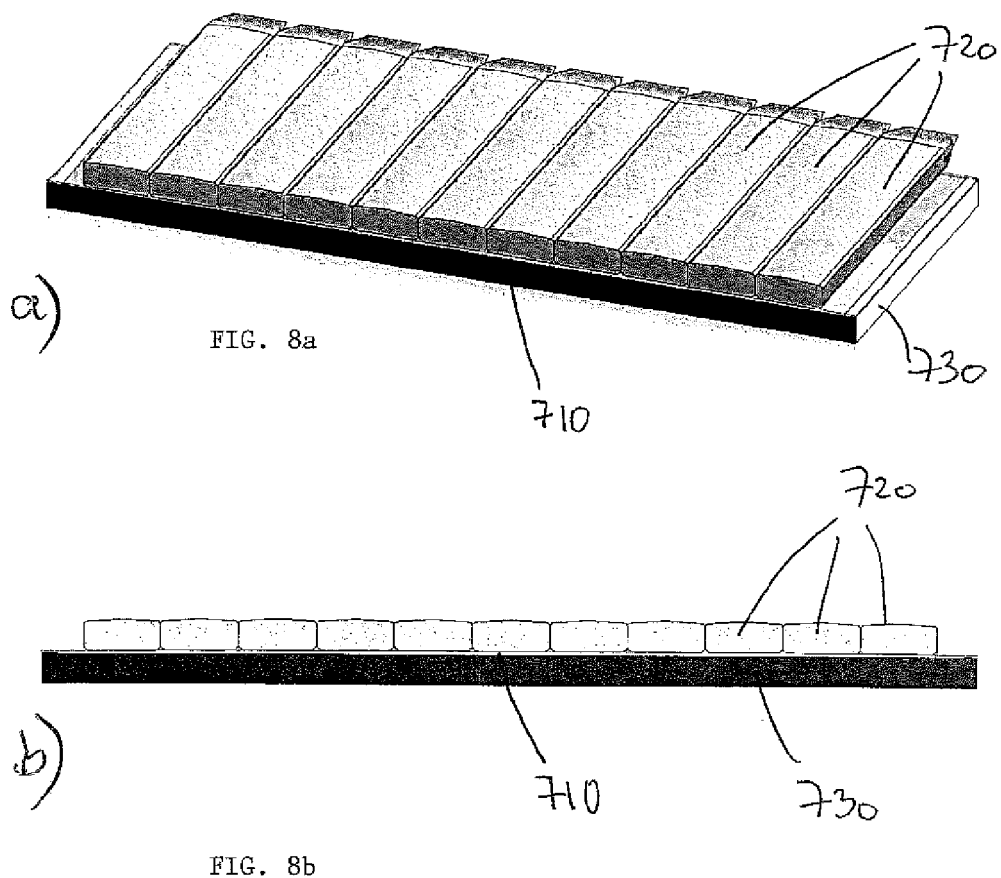

FIG. 8a provides a perspective view of a section of a thin film photobioreactor panel in which an inflatable thermal control layer 710 (e.g., a flexible polymeric enclosure) is in a deflated state (e.g., air significantly removed from an air bladder) to provide increased thermal contact of the array of linked reactor chambers 720 (e.g., enclosures made of polymeric material) with the heat energy system 730 (typically functioning as a thermal sink during day-time operation and as heat source during night-time operation). The corresponding cross-sectional view is shown in FIG. 8b.

A "spectrum of electromagnetic radiation" as used herein, refers to electromagnetic radiation of a plurality of wavelengths, typically including wavelengths in the infrared, visible and/or ultraviolet light. The electromagnetic radiation spectrum is provided by an electromagnetic radiation source that provides suitable energy within the ultraviolet, visible, and infrared, typically, the sun.

The photobioreactors of the present invention are adapted to support a biologically active environment that allows chemical processes involving photosynthesis in organisms such as phototrophic organisms to be carried out or biochemically active substances to be derived from such organisms. The photobioreactors can support aerobic or anaerobic organisms.

The photobioreactors can include one or more reactor chambers. Typically, the photobioreactors comprise a plurality of reactor chambers, for example, between 2 and 40, and, more typically, between 5 and 30. The photobioreactor panels can be of different shape (e.g., elongated semi-circle shaped, flat, etc.) and size. Typically, however, they are substantially flat. This can be advantageous, for example, for positioning of the panels on flat surfaces such as flat ground or a body of water, for example, a lake. Photobioreactor panels of any size are suitable for the present invention. However, typically, photobioreactor panel size is influenced by the material and manufacturing choices. For example, in some embodiments of the present invention, the photobioreactor panels are made of a thin film polymeric material such as the one shown in FIG. 1 which can be, for example, between 1 and 100 meters long. In preferred embodiments, the photobioreactor panel is 1 meter wide (e.g., 19 segments each about 5 cm wide) and 40 meter long. A further consideration is transportability of a manufactured photobioreactor panel or photobioreactor, which is greatly enhanced by using flexible thin-film photobioreactor panels that can be at least to some extent folded and/or rolled. For photobioreactors including very large photobioreactor panels this is a significant advantage, because it can prevent costly transportation permits and oversized transport vehicles, or, alternatively, significant installation costs at the installation site, Typically, for flat photobioreactor panels, the width is between about 10 cm and 5 m, more typically, the width is between 50 cm and 3 m.

Each reactor chamber of a photobioreactor can be of a different shape and dimension. Typically, however, in photobioreactors including a plurality of reactor chambers, the reactor chambers are of similar or identical shape and dimensions, for example, channels positioned in parallel with substantially longer channel length than width. Various reactor chamber cross sections are suitable, for example, rectangular, cylindrical, or half-elliptical as shown in FIGS. 1-8. Preferably, the reactor chamber is half-elliptical or rectangular. Further, reactor chamber(s) can be enclosures (e.g., bags) welded from thin polymeric films. Such reactor chambers can allow for advantageous compact transport, facilitate sterilization (e.g., with radiation such as gamma radiation) prior to deployment, and allow use as disposable reactor chamber(s) because of the cost-efficiency and/or energy efficiency of their production. They can also be reused.

Phototrophic microorganisms contained in photobioreactors for their growth and/or the production of carbon-based products of interest, require light. Therefore, the photobioreactors, and, in particular, the reactor chambers are adapted to provide light of a wavelength that is photosynthetically active in the phototrophic microorganism to reach the culture medium. Typically, at least part of the reactor chamber is transparent for light of a wavelength that is photosynthetically active in the phototrophic microorganism. This can be achieved by proper choice of the material, for example, thin-film material for the reactor chamber to allow light to enter the interior reactor chamber.

Typically, the reactor chamber(s) of the photobioreactor are adapted to allow cultivation of the phototrophic microorganisms in a thin layer. Typically, the layer is between about 5 mm and about 30 mm thick, and, more typically, between about 10 mm and about 15 mm.

Typically, the photobioreactor panels described herein are placed on the ground or float on water such that reactor chamber(s) are directed upwards and the heat energy system, e.g., heat exchange chamber(s) are placed on the ground. Preferably, the heat exchange chambers are embedded, at least in part, in the ground to increase the passive thermal contribution to the thermally controlled operation of the photobioreactors. In the case of embodiments to floating photobioreactors, the heat energy system is surrounded, at least in part, by water.

Alternatively, the photobioreactor(s) can also be placed above the ground using solid support structures, for example, made of metal, mesh or fabric.

The photobioreactors can be operated in batch, fed batch or continuous mode.

The photobioreactors of the present invention can include a number of devices that can support the operation of the photobioreactors. For example, devices for flowing gases (e.g., carbon dioxide, air, and/or other gases), measurement devices (e.g. optical density meters, thermometers), inlets and outlets, and other elements can be integrated or operationally coupled to the photobioreactor panels described herein.

Typically, the photobioreactor will include one or more pumps to establish culture flow through the reactor chamber(s) during operation; this also allows placement of the photobioreactors over non-flat land thereby increasing the land area available without major reworking.

Further, the photobioreactor panels can be adapted to allow gas flow through the reactor volumes. Gas (e.g. $CO_2$) flow can be co- and/or counterdirectional to liquid flow through the reactor chamber(s) of the photobioreactor. For example, in certain embodiments, the photobioreactors are adapted to allow codirectional gas flow in one part of the reactor chamber and counterdirectional gas flow in another part of the reactor chamber. In other embodiments, one or more reactor chambers of a photobioreactor are adapted to allow codirectional gas flow, and one or more other reactor chambers of the photobioreactor are adapted to allow counterdirectional gas flow.

Phototrophic organisms growing in photobioreactors can be suspended or immobilized.

Suitable photobioreactors for the present invention are closed bioreactors, as contrasted with open bioreactors, such as a pond or other open body of water, open tanks, open channels, etc. Typically, the photobioreactors have a plurality of channels in fluid communication.

Heat energy systems as used herein are systems that can function as a heat sink and heat reservoir. Typically, the heat energy system includes a material with sufficiently high heat capacity. The material can be solid, for example, a metal or polymer or liquid, preferably, water. Preferably, the heat energy system includes a heat exchange chamber containing a heat exchange liquid such as water, and, optionally, inlets and outlets for exchange of the heat exchange liquid.

As used herein, "light of a wavelength that is photosynthetically active in the phototrophic microorganism" refers to light that can be utilized by the microorganism to grow and/or produce carbon-based products of interest, for example, fuels including biofuels.

"Biofuel" refers to any fuel that derives from a biological source, including one or more hydrocarbons, one or more alcohols, one or more fatty esters or a mixture thereof. Typically, ethanol or other liquid hydrocarbon fuels can be produced.

"Carbon-based products of interest" include alcohols such as ethanol, propanol, isopropanol, butanol, fatty alcohols, fatty acid esters, ethyl esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ϵ-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

"Phototrophs" or "photoautotrophs" are organisms that carry out photosynthesis such as, eukaryotic plants, algae, protists and prokaryotic cyanobacteria, green-sulfur bacteria, green non-sulfur bacteria, purple sulfur bacteria, and purple non-sulfur bacteria. Phototrophs include natural and engineered organisms that carry out photosynthesis and hyper-light capturing organisms.

As used herein, "organisms" encompasses autotrophs, phototrophs, heterotrophs, engineered light capturing organisms and at the cellular level, e.g., unicellular and multicellular.

A "biosynthetic pathway" or "metabolic pathway" refers to a set of anabolic or catabolic biochemical reactions for converting (transmuting) one chemical species into another. For example, a hydrocarbon biosynthetic pathway refers to the set of biochemical reactions that convert inputs and/or metabolites to hydrocarbon product-like intermediates and then to hydrocarbons or hydrocarbon products. Anabolic pathways involve constructing a larger molecule from smaller molecules, a process requiring energy. Catabolic pathways involve breaking down of larger molecules, often releasing energy.

As used herein, "light" generally refers to sunlight but can be solar or from artificial sources including incandescent lights, LEDs, fiber optics, metal halide, neon, halogen and fluorescent lights.

Throughout this specification and claims, the word "comprise" or variations such as "comprises" or "comprising", will be understood to imply the inclusion of a stated integer or group of integers but not the exclusion of any other integer or group of integers.

Further embodiments of the present invention are directed to solar gathering systems including a photobioreactor as described above.

The photobioreactors and solar energy gathering systems of the present invention allow temperature control in a cost effective manner, reducing the energy required for temperature control of a culture medium containing phototrophic microorganisms. The photobioreactors and solar energy gathering systems are designed to benefit significantly from passive thermal cooling and heating thereby reducing or eliminating the need for active cooling and heating. In certain embodiments, the photobioreactor is a thin-film photobioreactor adapted for horizontal (flat) placement on the ground or for floating on water. In addition to benefiting from the heat sink/reservoir potential of the ground or the water on which the photobioreactor is placed or floats, respectively, such placement has the advantage that less structural support for the photobioreactor is required. Further, using thin-film polymeric materials requires less polymeric material per unit area of photobioreactor panel. Further, flexibility of photobioreactor panels reduces transportation costs and simplifies large photobioreactor installations. Thin-film polymeric photobioreactor panels can also be manufactured to very large dimensions which can further reduce cost. In preferred embodiments of the present invention, controllable thermal contact is provided by controllable inflation of an inflatable thermal control layer, such as a flexible polymeric enclosure. Typically, the inflatable thermal control layer can be inflated with a fluid. Preferably, the fluid has low thermal conductivity. The fluid can be a liquid or a gas such as air. Inflating the inflatable thermal control layer with the fluid typically leads to increasing thickness of the inflatable thermal control layer, and thus, greater spatial separation of reactor chamber(s) and the heat energy system (typically acting as thermal sink during day-time operation and as heat source during night-time operation). Thus, typically, with increasing inflation the thermal isolation between the reactor chamber(s) and the heat energy system increases. Typically, the flexible thermal control layer is placed in between reactor chamber(s) and the heat energy system. Preferably, one inflatable thermal control layer is positioned in between the reactor chamber(s) (if a plurality of reactor chambers is used, as is preferred, then preferably all reactor chambers abut the inflatable thermal control layer) and the heat energy system.

In further preferred embodiments, reactor chamber(s) are flexible, for example, to adapt to the controllable inflation of an inflatable thermal control layer. Also, the reactor chambers can be designed to be compactable when empty (i.e., substantially without culture medium and gases), and form raised enclosures in the presence of significant amounts of culture medium in the reactor chambers, that is, amounts that are typically to be expected during operation of the photobioreactor. The raised enclosures that can be formed are not limited to a particular cross-section, however, a preferred cross-section is substantially rectangular as shown, for example, for the reactor chambers 720 in FIGS. 7b and 8b.

In other preferred embodiments, the heat energy system can be a separating layer between the ground or water on which the photobioractor is placed or floats. Typically, the separating layer is adapted to allow significant heat transfer between the ground or water and the thermal control layer.

A further preferred embodiment of the present invention is a photobioreactor (alone or as part of a solar energy gathering system) as described above, but without a heat energy system, that is, the reactor chamber(s) of the photobioreactor are in controllable thermal contact with the ground or water on which the photobioreactor is positioned. For example, one or more inflatable thermal control layers can be placed in between the reactor chamber(s) of the photobioreactor and the ground or water.

In further preferred embodiments the inflatable thermal control layer (e.g., the thermal control layer 710) can also be adapted to be inflated with a liquid providing significant thermal conductivity. Such liquids can establish significant thermal contact of the reactor chamber(s) with the heat energy system, and/or ground or water (in the absence of a heat energy system). Thermal isolation of the reactor chamber(s) from the heat energy system, and/or ground or water can then be achieved by draining out the liquid, that is, with a deflated thermal control layer. Use of an inflatable thermal contact layer with a liquid as described above, can reduce, partly or entirely, the thermal contact resistance during the desired heat transfer phase, and benefits from the thermal contact resistance in the drained state to improve thermal isolation when it is desired.

In alternative embodiments, the inflatable thermal control layer (e.g., the thermal control layer 710) can be sectioned to provide a plurality of volumes (for example, two volumes, but typically not more than 100 volumes, more typically, not more than 10 volumes) that can be filled separately with liquid. In these embodiments, the inflatable thermal control layer can further be adapted to provide a tilt of the reactor chamber(s) when the inflatable thermal control layer volumes are filled to different extents with the liquid. The inflatable thermal control layer can be adapted to cause the tilt due to lifting of the reactor chamber(s) above the inflating volumes and/or due to rolling (without wanting to be bound by theory, the weight of the liquid in filled volumes/sections can lead to a momentum that can lead to rolling and, hence orienting of the reactor chamber(s)) of the inflatable thermal control layer upon inflating the volumes to different extents. For example, in the case of an inflatable thermal control layer sectioned into two volumes of equal size (i.e., a first and a second volume), inflation of the first volume with more liquid than in the second volume can lift the reactor chamber(s) above the first volume relative to the reactor chamber(s) above the second volume thereby tilting the reactor chamber(s) to a side. Accordingly, inflatable thermal control layers having a plurality of volumes that can be separately filled with liquid provide not only controllable thermal contact of the reactor chamber(s) with the heat energy system, and/or ground or water, but also controllable alignment of the reactor chamber(s) to control exposure to the light source, typically, the sun. For example, the reactor chamber(s) could be tilted to the east in the morning and to the west in the evening. Further, liquids of different thermal conductivity can be used in the different volumes of the inflatable thermal control layer.

An example embodiment of this is shown in FIG. 9a, which provides a perspective view of a section of a photobioreactor panel in which an inflatable sectioned (with three volumes) thermal control layer 900 is filled with a liquid to allow thermal contact of an array of linked reactor chambers 720 with a heat energy system 730. The heat energy system 730 can be part of the photobioreactor, or it is the ground or water, or another surface on which the photobioreactor is placed. FIG. 9b provides a cross-sectional view of the photobioreactor panel in FIG. 9a. FIG. 9c provides a cross-sectional view of the photobioreactor panel in FIG. 9a, in which the sections/volumes are filled to different extents leading to a tilt of the reactor chambers.

In further embodiments, the heat energy system (e.g. 730) can be or include a plurality of inflatable heat exchange chambers that can be filled separately with liquid. In these embodiments, the inflatable heat exchange chambers can further be adapted to provide a tilt of the reactor chamber(s) when the inflatable heat exchange chambers are filled to different extents with the liquid. For example, in the case of two heat exchange chambers of equal size (i.e., a first and a second chamber), inflation of the first chamber with more liquid than in the second chamber can lift the reactor chamber(s) above the first chamber relative to the reactor chamber(s) above the second chamber thereby tilting the reactor chamber(s) to a side. Accordingly, a heat energy system including inflatable heat exchange chambers that can be separately filled with liquid provide controllable alignment of the reactor chamber(s) to control exposure to the light source, typically, the sun. These heat energy systems can also be used in combination with the inflatable thermal control layers described in the preceding paragraph.

An example embodiment of this is shown in FIG. 10a which provides a perspective view of a section of a photobioreactor panel in which an inflatable thermal control layer 710 is sandwiched between reactor chambers 720 and a heat energy system 1000 including three inflatable heat exchange chambers that can be filled separately with liquid. FIG. 10b provides a cross-sectional view of the photobioreactor panel in FIG. 10a. FIG. 10c provides a cross-sectional view of the photobioreactor panel in FIG. 10a, in which the sections/volumes of the heat energy system are filled to different extents leading to a tilt of the reactor chambers. The solar energy gathering systems, for example, photobioreactors, as described herein, can be sterilized with vaporized hydrogen peroxide, ozone, ozonated water, sodium hydroxide, and/or with radiation. Typically, vaporized hydrogen peroxide is used to sterilize the inner surfaces of the photobiorector, and, optionally, all attached peripheral pieces. The sterilization methods can be used for photobioreactors, photobioreactor arrays and systems that contain low service temperature materials for which the use of conventional sterilization methods such as steam application is not possible.

It has been found that vaporized hydrogen peroxide can be applied to sterilize photobioreactors, photobioreactor arrays and systems to allow cultivation of microorganisms while preventing (or inhibiting/reducing) significant contamination for a substantial time.

The solar energy gathering systems (e.g., photobioreactors) of the present invention are made from materials that allow sterilization with vaporized hydrogen peroxide, ozone, ozonated water, sodium hydroxide, and/or radiation, without substantial material degradation over time.

Another embodiment of the present invention is a method for producing carbon-based products of interest comprising: (a) sterilizing a solar energy gathering system (e.g., photobioreactor) as described herein using vaporized hydrogen peroxide, ozone, or radiation; and (b) culturing microorganisms in the solar energy gathering system (e.g., photobioreactor) to produce carbon-based products of interest.

Figure 14:
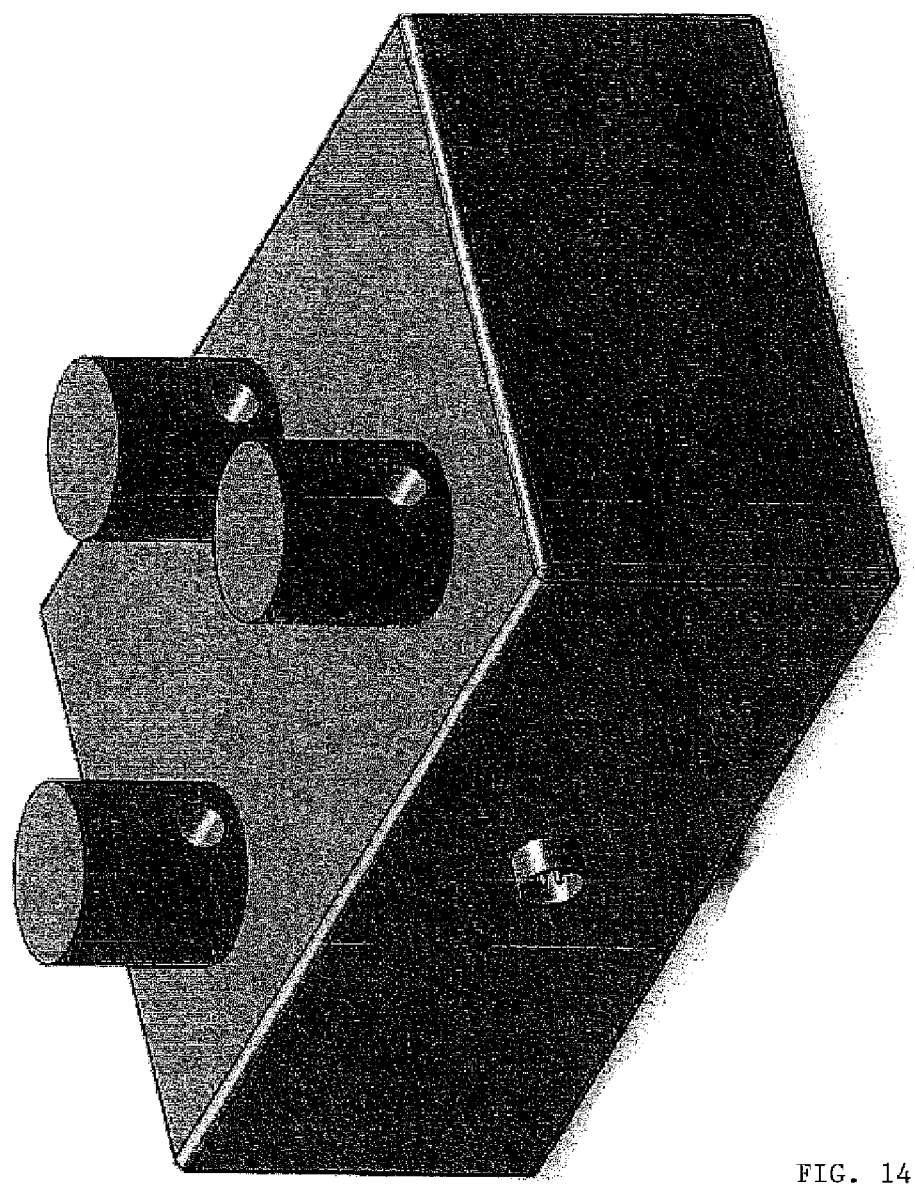
FIG. 14 is a illustration of a solenoid box applied in the control of the sterilization of photobioreactors. The drawings are not necessarily to scale, emphasis instead being placed upon illustrating embodiments of the present invention.

Typically, the solar energy gathering systems (e.g., photobioreactors) of the present invention are adapted to prevent (reduce or inhibit) non-sterile air introduction into the solar energy gathering system (e.g., photobioreactor) during media additions or sampling. A further embodiment of the present invention is directed to a method for sterilizing the photobioreactors of the present invention. The method comprises coordinating the opening and closing of valves, inlets and outlets of the photobioreactor using a solenoid box. FIG. 14 provides an illustration of an apparatus employed in the sterilization method to help ensure that non-sterile air is not introduced into the reactor during media additions and sampling The sterilization methods of the present invention require are time effective and allow prevention or at least mitigation of outcompetion by undesired species such as bacteria, fungi, protozoa or other algal species, thereby leading to insubstantial presence of contaminants during typical operation durations. Sterilization can also allow early exponential growth of the inoculum during its growth. During the initial lag phase and the early part of the exponential growth phase, the culture can be at high risk to be outcompeted by contaminants such as *Pseudomonas* or *Microbacterium*. Thus, effective sterilization methods can ensure the culturing of only desired species in the photobioreactor. After reaching a certain optical density, the risk of contamination and competition from other species is lowered. Additionally, the effect of sterilization can lead to monoculture, enabling increased productivity of products.

STERILIZATION EXAMPLES

Sterilization of PBRs Using Vaporized Hydrogen Peroxide

Figure 11:
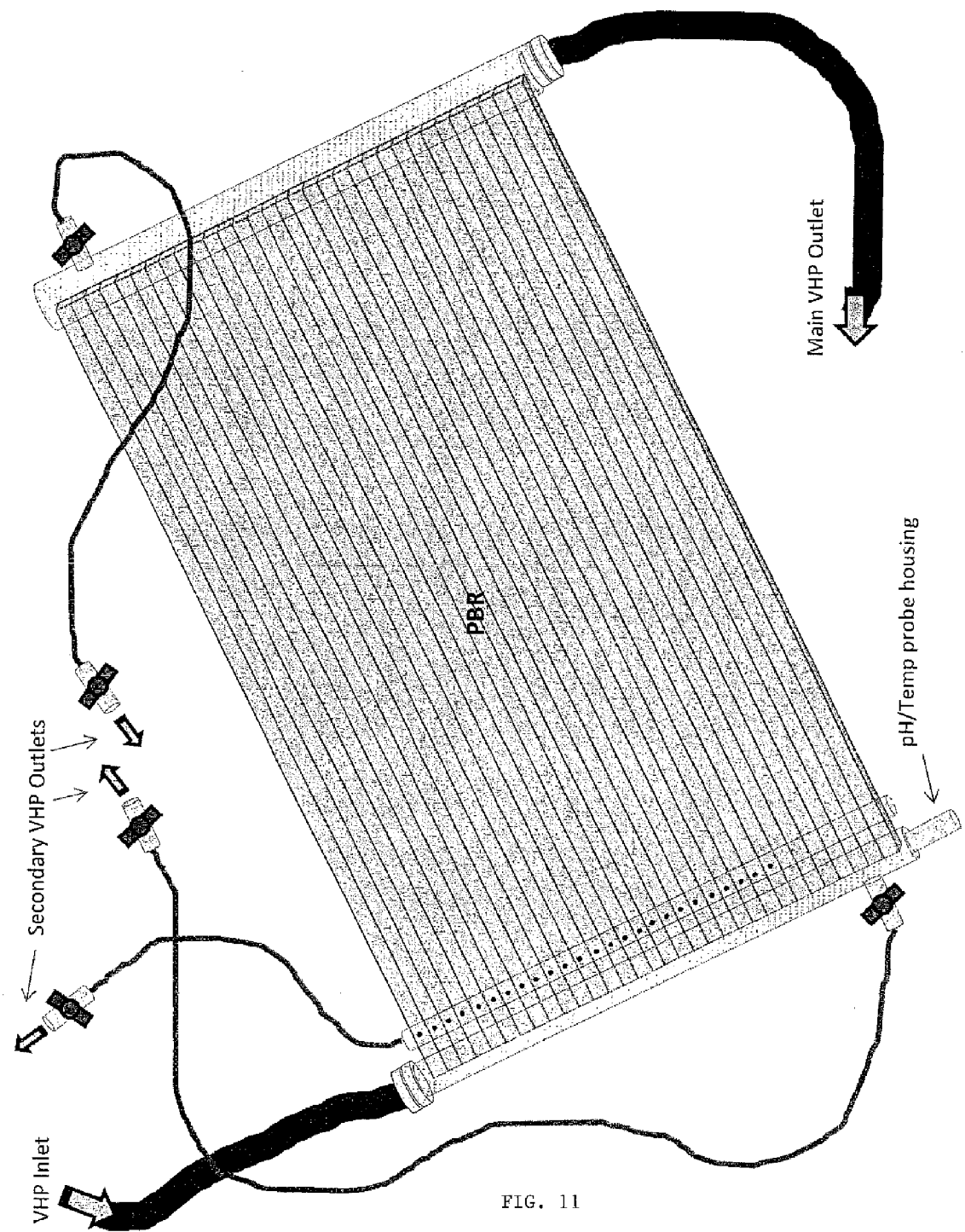
FIG. 11 is a diagram depicting sterilization setup for a photobioreactor using vaporized hydrogen peroxide.

The use of a vapor sterilization for a photobioreactor is shown in FIG. 11.

The interior of the photobioreactor was cleaned and dried. Humidity within the PBR was lowered to below the hydrogen peroxide dew point. The hydrogen peroxide was vaporized via a vaporization device, such as the Steris "VHP ARD Mobile" unit. The vaporized HP was blown into the PBR at a controlled rate such that all biological agents within the reactor are killed (i.e. $\geq 400$ ppm for $\geq 30$ minutes). The vaporized HP was not allowed to exceed its dew point through-out this entire procedure. Following fumigation, the VHP was vented out of the bioreactor until VHP levels were $\leq 1$ ppm. Effectiveness of the sterilization procedure can be demonstrated with the use of Biological Indicators (BIs) placed within the Bioreactor prior to initiating sterilization.

Biological indicators can be placed within various locations within the PBR. The PBR is then subjected to the sterilization process. Following sterilization the BIs are removed and placed into culture media. If there is no growth then the BIs have been deactivated. Each BI has 106 organisms on it. No growth indicates $\geq 6$ log reduction.

Sterilization Setup Using Ozone

A 8 mm photobioreactor has been successfully sterilized via the ozone procedure.

Figure 12:
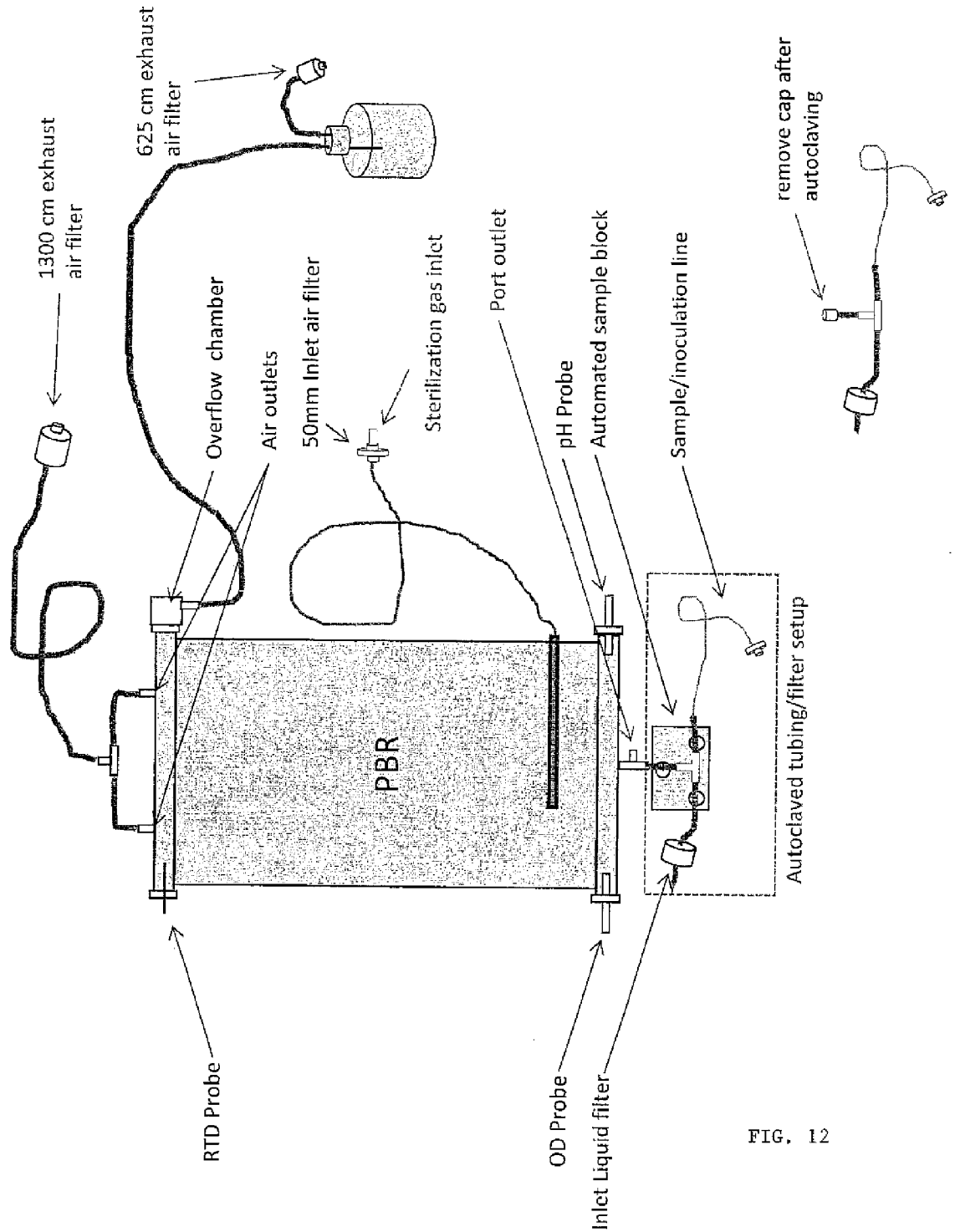
FIG. 12 is a diagram illustrating sterilization setup for photobioreactors.

A photobioreactor was setup as indicated in FIG. 12. The tubing/filter set up was prepared as follows and autoclaved (30 minutes @ 121° C.) prior to initiation of the sterilization procedure. The sterile tubing/filter setup (FIG. 12) was fitted into the automated sample block. Then, all solenoids on the sample block were closed and verified. The cap was then removed and the open end was fitted into the bottom of the "Port Outlet". The sample block was used to help ensure that non-sterile air was not introduced into the reactor during media additions and sampling. This is achieved by coordinating the opening of the correct valves and timing the closings. Exhaust lines were connected to the outlet side of the 625 cm2 bottle vent filter, and the outlet side of the 1300 cm2 exhaust air filter. Both exhaust lines were fitted together and the common line is fed into a dryer and then into the ozone destruct module (FIG. 13).

Sterilization Procedure Using Ozone

Figure 13:
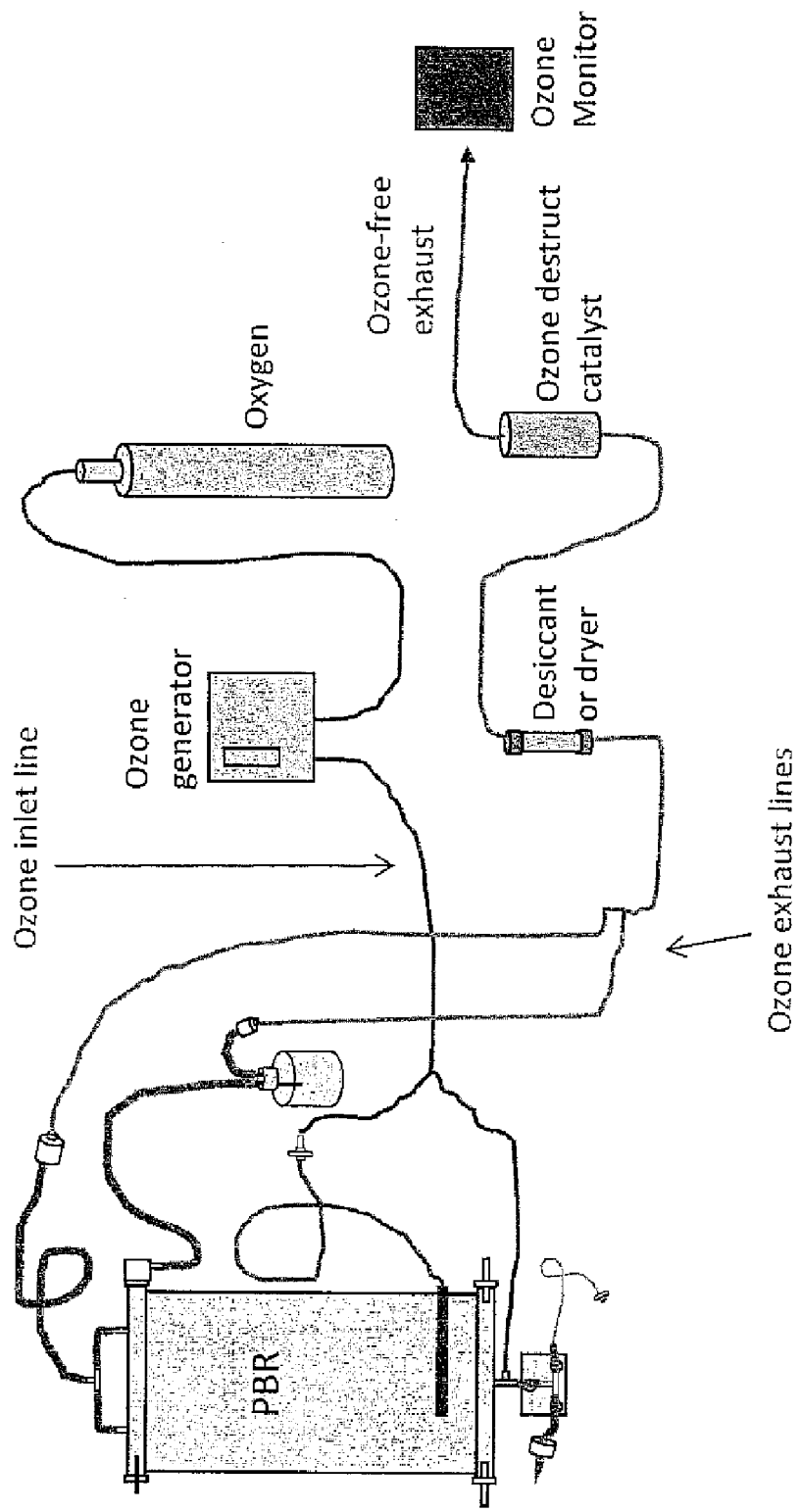
FIG. 13 is a diagram depicting sterilization setup for a photobioreactor using ozone.

FIG. 13 provides an illustration of a PBR connected to ozone for sterilization. A line from the ozone generator (which is fed by an oxygen tank) was connected to the air inlet filter and the side port of the "Port Outlet". The Port Outlet line was closed by pinching with a screw clamp (or similar). Approximately 200-400 mL of de-ionized water was added to the PBR. The oxygen feed was turned on and the flow rate was set to 2-5 Liters per minute. The clamp on the Port Outlet line was unpinched just enough to see bubbles forming in the bottom header. The oxygen flow rate was readjusted as necessary. The system was checked for leaks with an O2 meter and/or a dilute liquid detergent applied to connections. When the system was verified to be functioning properly the ozone generator was switched on. All of the connections were immediately re-checked for leaks with the ozone monitor. These connections were also periodically checked during the course of the sterilization. The ozone destruct exhaust was also check frequently to verify that the catalyst was functioning properly. Ozonation was conducted for approximately 3 hours. Following the ozonation period the clamp on the Port Outlet was closed. This port was closed before turning off the ozone generator in order to avoid unsterilized/unfiltered gas from entering the PBR. The ozone generator was then turned off. Oxygen was allowed to continue to blow through the inlet filter for a few minutes and then it was also shut off. No gas was blowing through the system. The line on the non-sterile side of the closed thumb screw clamp was disconnected. The unit was typically left in place for ~12 hours to allow any residual ozone in the PBR to react. If the unit must be moved before the 12 hour wait period, the lines should be clamped first. The tube on the sterile side of the inlet air filter was clamped and the ozone line from the non-sterile side removed. The tubes on the sterile side of the 625 cm2 bottle filter and the 1300 cm2 exhaust air filter were clamped. Then the lines from these filters were removed. After the unit has set for >12 hours the clamps are no longer needed. Maintaining sterility, drain the water from the reactor before charging it with culture medium.

Culturing Cyanobacteria in the Sterilzed PBR

After ozone sterilization of the PBR as described above, an inoculum containing Synechococcus 7002 was introduced in the PBR. Contaminant-free growth of the inoculums was noted for 2 weeks.

The relevant teachings of all patents, published patent applications and literature references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for thermal control of a culture medium containing a phototrophic organism for the production of a fuel or carbon-based product in a photobioreactor, the method comprising:
    (a) measuring the temperature of the culture medium contained in a reactor chamber of the photobioreactor, the reactor chamber being positioned substantially horizontally to provide a headspace above the culture medium and being one of a plurality of channels positioned in parallel and having a substantially longer length than width; wherein at least part of the reactor chamber is transparent for light of a wavelength that is photosynthetically active in the phototrophic microorganism;
    (b) measuring the temperature of a heat exchange liquid contained in a heat exchange chamber, the heat exchange liquid being in controllable thermal contact with the culture medium in the reactor chamber through a separating layer;
    (c) determining if a change in thermal contact between the culture medium and the heat exchange liquid is desired; and
    (d) controlling the thermal contact between the culture medium and the heat exchange liquid by controlling the extent of a gas space above the heat exchange liquid in the heat exchange chamber; wherein the gas space is thermally insulating.

2. The method of claim 1, wherein controlling the extent of the gas space above the heat exchange liquid in the heat exchange chamber comprises eliminating or decreasing the extent of the gas space above the heat exchange liquid in the heat exchange chamber to increase thermal contact between the culture medium and the heat exchange liquid.

3. The method of claim 1, wherein controlling the extent of the gas space above the heat exchange liquid in the heat exchange chamber comprises forming or increasing the extent of the gas space above the heat exchange liquid in the heat exchange chamber to reduce thermal contact between the culture medium and the heat exchange liquid.

4. The method of claim 1, wherein the heat exchange liquid functions as a heat sink and a heat source.

* * * * *